(12) United States Patent
Ona et al.

(10) Patent No.: US 10,413,276 B2
(45) Date of Patent: Sep. 17, 2019

(54) ULTRASONIC PROBE

(71) Applicant: Toshiba Medical Systems Corporation, Otawara-shi (JP)

(72) Inventors: Yasuhiro Ona, Nasushiobara (JP); Hiroyuki Shikata, Nasushiobara (JP); Satoru Tezuka, Nasushiobara (JP); Satoru Asagiri, Tokyo (JP); Michiko Oishi, Tokyo (JP)

(73) Assignee: Canon Medical Systems Corporation, Otawara-shi (JP)

( * ) Notice: Subject to any disclaimer, the term of this patent is extended or adjusted under 35 U.S.C. 154(b) by 882 days.

(21) Appl. No.: 14/860,043

(22) Filed: Sep. 21, 2015

(65) Prior Publication Data

US 2016/0007964 A1 Jan. 14, 2016

Related U.S. Application Data

(63) Continuation of application No. PCT/JP2014/057123, filed on Mar. 17, 2014.

(30) Foreign Application Priority Data

Mar. 21, 2013 (JP) ................. 2013-058866

(51) Int. Cl.
*A61B 8/00* (2006.01)
*B06B 1/06* (2006.01)
*G01S 15/89* (2006.01)

(52) U.S. Cl.
CPC .......... *A61B 8/4494* (2013.01); *A61B 8/4444* (2013.01); *B06B 1/0629* (2013.01); *G01S 15/8927* (2013.01); *A61B 8/4483* (2013.01)

(58) Field of Classification Search
CPC ... A61B 8/4444; A61B 8/4483; A61B 8/4494; B06B 1/0629; G01S 15/8927
See application file for complete search history.

(56) References Cited

U.S. PATENT DOCUMENTS

2007/0244392 A1 10/2007 Tezuka
2008/0178677 A1 7/2008 Baumgartner et al.

FOREIGN PATENT DOCUMENTS

JP 62-098791 A 5/1987
JP 2004-056504 A 2/2004
(Continued)

OTHER PUBLICATIONS

International Search Report dated Jun. 10, 2014 in PCT/JP2014/057123 filed Mar. 17, 2014, with English translation.
(Continued)

*Primary Examiner* — Michael T Rozanski
(74) *Attorney, Agent, or Firm* — Oblon, McClelland, Maier & Neustadt, L.L.P.

(57) ABSTRACT

An ultrasonic probe includes an ultrasonic transducer array and a multilayer body for extracting an electric wiring from each electrode. Transducers are classified into at least a first group and a second group. The multilayer body includes a first FPC layer on which the array is stacked and a second FPC layer on which the first FPC layer is stacked. The first FPC layer and the second FPC layer include upper surface connection pads and lower surface electrode pads which maintain a uniform level at positions spatially corresponding to the respective transducers. FPC layers constituting an FPC multilayer body are bonded to each other to be integrally formed in a region corresponding to the width of the array. On the other hand, the respective FPC layers are not bonded to each other and separated from each other outside the region corresponding to the width of the array.

14 Claims, 10 Drawing Sheets

(56) References Cited

FOREIGN PATENT DOCUMENTS

| | | |
|---|---|---|
| JP | 2004-112326 A | 4/2004 |
| JP | 2006-110140 A | 4/2006 |
| JP | 2008-183402 A | 8/2008 |
| JP | 2011-250119 A | 12/2011 |
| JP | 2012-065914 A | 4/2012 |

OTHER PUBLICATIONS

Written Opinion dated Jun. 10, 2014 in PCT/JP2014/057123 filed Mar. 17, 2014.

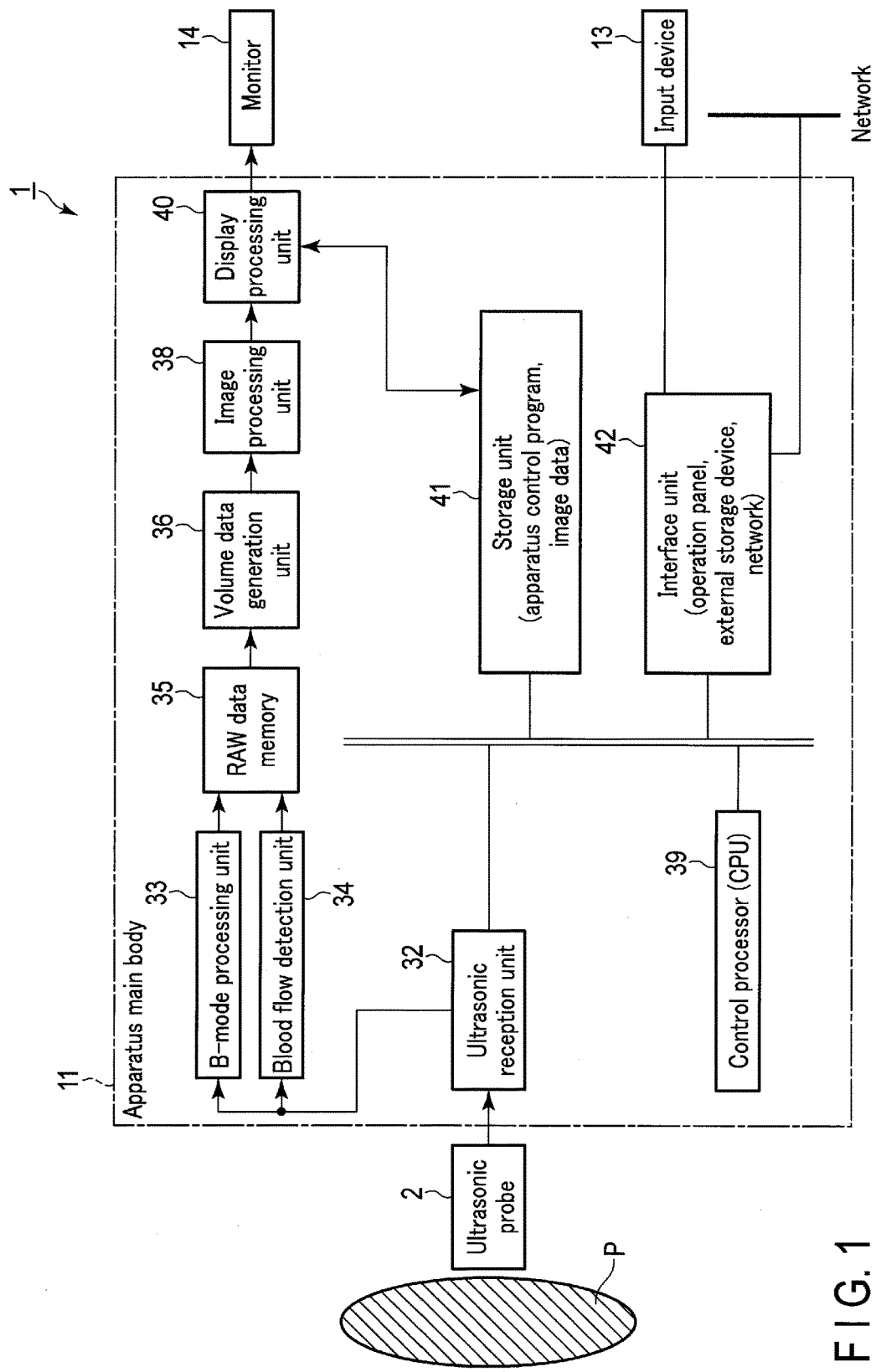
F I G. 1

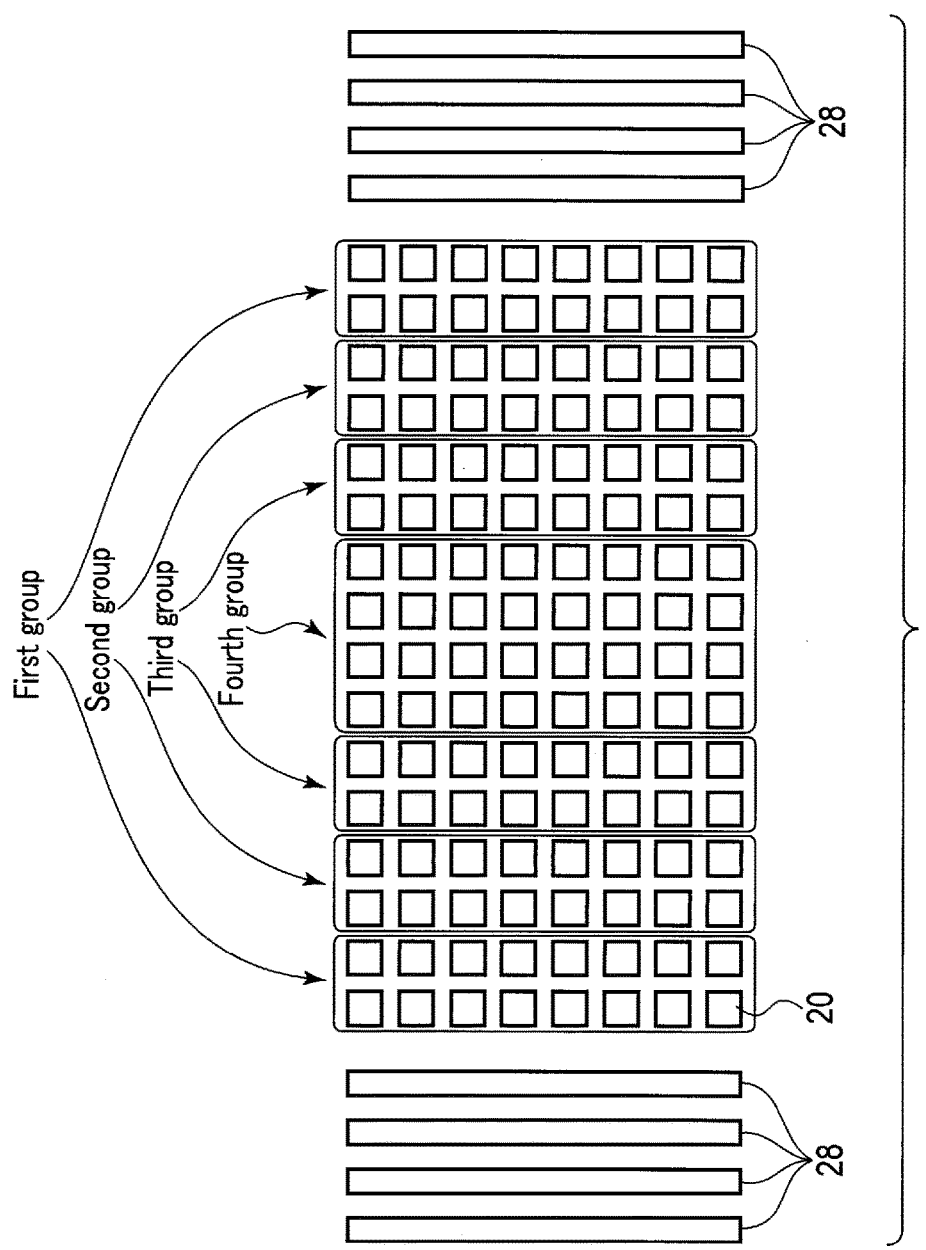
F I G. 4

ULTRASONIC PROBE

This application is a Continuation Application of PCT Application No. PCT/JP2014/057123, filed Mar. 17, 2014 and based upon and claims the benefit of priority from the Japanese Patent Application No. 2013-058866, filed Mar. 21, 2013, the entire contents of all of which are incorporated herein by reference.

FIELD

Embodiments described herein relate generally to an ultrasonic probe.

BACKGROUND

Ultrasonic probes used for ultrasonic diagnostic apparatuses and the like include an array ultrasonic probe formed from an array of a plurality of ultrasonic transducers. Recently, a two-dimensional array probe formed from a two-dimensional array of a plurality of ultrasonic transducers has appeared on the market to allow three-dimensional scanning on a diagnosis target region of an object. Such a two-dimensional array probe includes an enormous number of elements, and hence generally incorporates electronic circuitry for transmission/reception in the probe grip portion. For example, electronic circuitry in the probe incorporates, as a function, part of transmission/reception used by the diagnostic apparatus main body.

When using such a two-dimensional array probe, since the probe includes an enormous number of ultrasonic transducers (i.e., channels), the number of wirings required for transmission/reception between the ultrasonic probe and the ultrasonic diagnostic apparatus main body tends to be enormous. In order to prevent this, for example, an attempt has been made to provide electronic circuitry for generating transmission pulses in the ultrasonic probe instead of the ultrasonic diagnostic apparatus main body so as to send out reception signals to the ultrasonic diagnostic apparatus main body upon accumulating a predetermined number of reception signals within the ultrasonic probe. In addition, there have been proposed a technique of commonly connecting a plurality of ultrasonic transducers via a switch capable of changing a connection pattern and collectively connecting a plurality of transducers to the transmission/reception circuitry of the diagnostic apparatus main body, a sparse technique of improving feasibility by decreasing the number of elements to be operated to decrease the number of connecting wires or electronic circuitry size, and the like (see FIG. 10).

In addition, there have conventionally been proposed several techniques of connecting electronic circuits to respective ultrasonic transducers provided in an ultrasonic probe. Typically, the following three techniques can be presented.

(1) An FPC (flexible printed circuit) is mounted on the rear surface of each ultrasonic transducer (element), and electronic circuits (ICs) are mounted on the FPC upon extraction of signal wires from the pattern of the FPC in the lateral direction or multiple point connection is performed on the board on which ICs are mounted.

(2) Signal wires vertically run into the backing and connected to the ICs mounted on the rear and side surfaces of the backing.

(3) ICs are directly connected to the rear surface of each ultrasonic transducer by using bumps and the like and connected to wirings in the FPC and the backing from the rear surfaces of the electronic circuits.

The technique (1) described above can be implemented at a low cost because of the simplicity of the structure of an ultrasonic probe, and exhibits a high degree of freedom of ICs. This can keep the cost of development low. On the other hand, the limitation of the pattern pitch of an FPC makes it impossible to make signals from elements in the middle portion of the array run through between the through holes of elements in the end portions of the array. FIG. 8 shows a case in which five wiring patterns run between adjacent through holes.

When using the technique (1) described above, however, if, for example, the element pitch is 0.4 mm×0.4 mm and the minimum pad diameter of each through hole is 0.1 mm, the gap between the pads is 0.3 mm. If, for example, wiring is performed with a wiring pitch of 40 µm, only seven patterns can be made to run between through holes. In addition, when patterns are to be extracted in the two directions of the array in this case, wirings can be extracted from only 16 rows of transducers. With 16 rows of transducers, the diameter is 6.4 mm. That is, a sufficient diameter cannot be obtained.

As an FPC structure, a multilayer FPC can be used, in which a wiring layer is provided on an inner layer to connect the surface layer to each layer via through holes. However, a multilayer FPC requires a complicated manufacturing process and a high cost, and has its limitation when arranging a fine pattern on the inner layer. In addition, a deterioration in the flexibility of the FPC itself will make it difficult to perform routing inside the probe grip portion or limit a connection portion for an electronic circuit board to one surface. This leads to an increase in connection area between the transducer array and the electronic circuit board. In some cases, in order to solve this problem, as shown in FIG. 9, the overall array is divided into a plurality of modules, and an FPC is provided for each module so as to form a structure having the FPCs sandwiched between the modules (in the above case, if, for example, an array is constituted by two modules, 32 rows of transducers are formed). In this case, the element pitch between the modules increases as compared with the original pitch to generate side lobes. In addition, if the position accuracy between the modules is low, the delay accuracy deteriorates. This affects images. It is, in particular, very difficult to keep the surface accuracy of the acoustic emission surface good. In addition, the division into modules will increase the numbers of components and processes, resulting in an increase in cost.

According to the technique (2) described above, it is difficult and costs much to manufacture a backing member through which an enormous number of signal wires run at a small pitch in the longitudinal direction. In addition, a backing member having such a structure causes a deterioration in the convergence of waveforms because of acoustic resonance, resulting in adverse effects on images. In addition, it is difficult for a soft material like a backing material to obtain sufficient flatness even by polishing. This leads to a deterioration in connection reliability with respect to the electrodes of IC chips.

The technique (3) described above needs to form pads on the two surfaces of electronic circuitry, which is difficult to implement by a general semiconductor process. Such a structure is formed by using a semiconductor process called through-silicon via. This is a special process, and hence leads to high cost of production.

In the technique (3), electrodes may be extracted from an IC end portion by wire bonding or the like while electrodes are exposed on one surface without using through-silicon via. However, this technique requires bonding pads and wiring spaces on both an IC and a board to increase acoustically ineffective portions. This inevitably causes an increase in the outer size of a probe. In addition, in order to prevent an IC (silicon semiconductor) from producing acoustically adverse effects, it is necessary to polish the IC chip itself to a very small thickness (e.g., 100 μm or less) and perform bare chip mounting. In such a case, it is difficult to handle ICs, and it is difficult to manufacture very thin chips in the case of through-silicon via.

In addition, since it is necessary to use a dedicated IC having a circuit size corresponding to an element array, the unit cost of ICs becomes high, and it is necessary to develop a dedicated ID (ASIC) for each use of an array. This also poses a problem in terms of development cost. Furthermore, the sparse technique shown in FIG. 10 leads to partial missing of elements, and hence exerts adverse effects on a sound field and sensitivity.

An ultrasonic probe having a structure like that shown in FIGS. 11 and 12 has also been proposed. However, it is necessary to additionally execute the step of forming level differences between FPCs and provide conductive layers having different thicknesses, resulting in a complicated manufacturing method.

As described above, the conventional techniques of connecting the electronic circuits to the respective ultrasonic transducers provided in the ultrasonic probe are not sometimes satisfactory in terms of manufacturing cost and product reliability.

BRIEF DESCRIPTION OF THE DRAWINGS

FIG. 1 is a block diagram of an ultrasonic diagnostic apparatus 1 provided with an ultrasonic probe according to an embodiment.

FIG. 4 is a plan view of the ultrasonic probe 2, to which an FPC multilayer body 22 having four FPC layers is applied, when viewed from the ultrasonic wave irradiation surface side (from the arrow A in FIG. 3).

DETAILED DESCRIPTION

Figure 2:
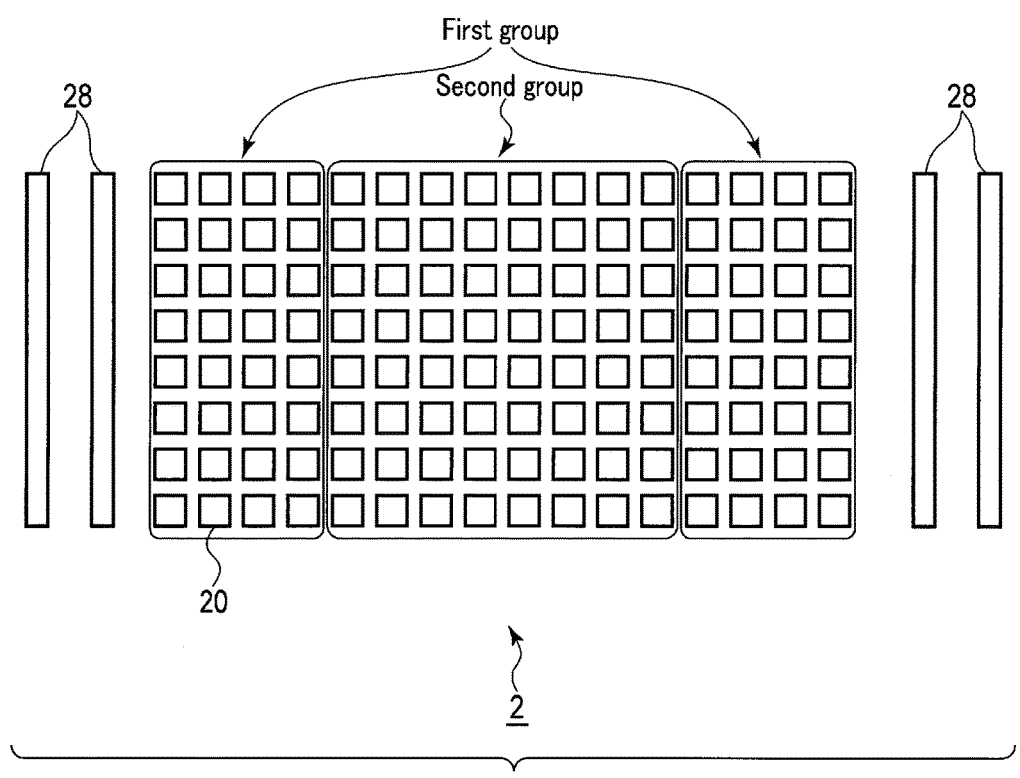
FIG. 2 is a plan view of an ultrasonic probe 2 according to this embodiment when viewed from the ultrasonic wave irradiation surface side (from an arrow A in FIG. 3).

According to one embodiment, there is provided an ultrasonic probe which comprises an ultrasonic transducer array formed by arraying a plurality of ultrasonic transducers provided with electrodes on end faces and a multilayer body configured to extract electric wirings from the respective electrodes. The plurality of ultrasonic transducers are classified into at least a first group and a second group. The multilayer body includes at least a first FPC layer on which the ultrasonic transducer array is stacked and a second FPC layer on which the first FPC layer is stacked. The first FPC layer includes at least a plurality of first upper surface connecting portions provided on an upper surface, on which the ultrasonic transducer array is stacked, so as to spatially correspond to the plurality of ultrasonic transducers, and electrically connected to the plurality of electrodes, a plurality of first lower surface connecting portions provided on a lower surface on an opposite side to the upper surface so as to spatially correspond to the plurality of ultrasonic transducers, a plurality of first through holes formed throughout from the upper surface to the lower surface so as to electrically connect the plurality of upper surface connecting portions connected to the electrodes of the ultrasonic transducers belonging to at least the second group to the plurality of first lower surface connecting portions, and the first signal wirings configured to extract electric wirings from the first upper surface connecting portions connected to the electrodes of the ultrasonic transducers belonging to the first group. The second FPC layer includes at least a plurality of second upper surface connecting portions provided on an upper surface, on which the first FPC layer is stacked, so as to spatially correspond to the plurality of ultrasonic transducers and electrically connected to the plurality of first lower surface connecting portions, a plurality of second lower surface connecting portions provided on a lower surface on an opposite side to the upper surface so as to spatially correspond to the plurality of ultrasonic transducers, and second signal wirings configured to extract electric wirings from the second upper surface connecting portions connected to the electrodes of the ultrasonic transducers belonging to the second group.

An embodiment will be described below with reference to the accompanying drawings. Note that the same reference numerals in the following description denote constituent elements having almost the same functions and arrangements, and a repetitive description will be made only when required.

FIG. 1 is a block diagram of an ultrasonic diagnostic apparatus 1 provided with an ultrasonic probe according to this embodiment. As shown in FIG. 1, the ultrasonic diagnostic apparatus 1 includes an ultrasonic probe 2, an input device 13, a monitor 14, an ultrasonic reception unit 32, a B-mode processing unit 33, a blood flow detection unit 34, a RAW data memory 35, a volume data generation unit 36, an image processing unit 38, a display processing unit 40, a control processor 39, a storage unit 41, and an interface unit 42.

The ultrasonic probe 2 is a device (probe) which transmits ultrasonic waves to an object and receives reflected waves from the object based on the transmitted ultrasonic waves. The ultrasonic probe 2 includes a plurality of ultrasonic transducers arrayed on its distal end, a matching layer, a backplane member (backing member), electronic circuitry (IC) which generates transmission pulses and supplies them to the respective ultrasonic transducers at predetermined timings, and electronic circuitry (IC) which reduces the number of reception signals to be sent out to the ultrasonic diagnostic apparatus main body side to a predetermined number by adding the reception signals generated by the respective ultrasonic transducers for each predetermined unit. The ultrasonic probe 2 is connected to an ultrasonic diagnostic apparatus main body 11 via a cable. The ultrasonic probe 2 according to this embodiment, in particular, includes an FPC multilayer body for electrically suitably connecting the respective electronic circuits described above to the respective ultrasonic transducers. The structure of the FPC multilayer body and a technique of electrically connecting the electronic circuits to the respective ultrasonic transducers by using the FPC multilayer body will be described in detail later.

Assume that the ultrasonic probe 2 according to this embodiment is a two-dimensional array probe (a probe having a plurality of ultrasonic transducers arrayed in a two-dimensional matrix). However, this example is not exhaustive. For example, an electric connection technique using an FPC multilayer (to be described later) can be applied to a one-dimensional array probe, a 1.5-dimensional array probe, a probe having a curved ultrasonic transmission/reception surface like a convex probe, and the like.

The input device 13 is connected to the apparatus main body 11 and inputs, to the apparatus main body 11, various types of instructions, conditions, an instruction to set a region of interest (ROI), various types of image quality condition setting instructions, and the like from an operator. The monitor 14 displays morphological information and blood flow information in the living body as images based on video signals from a display processing unit 27.

The ultrasonic reception unit 32 generates a signal (echo signal) having directivity by performing predetermined processing for a predetermined number of reception signals received from the ultrasonic probe 2. The B-mode processing unit 33 receives an echo signal from the reception unit 22, and performs logarithmic amplification, envelope detection processing, and the like for the signal to generate data whose signal intensity is expressed by a luminance level. The Doppler processing unit 34 obtains blood flow information such as mean velocities, variances, and powers as blood flow data at multiple points from the echo signals received from the reception unit 22, thereby generating blood flow data.

The raw data memory 35 generates raw data by using a plurality of data received from the B-mode processing unit 33 and the Doppler processing unit 34. The volume data generation unit 36 generates volume data by converting the RAW data into a data arrangement on a volume basis. The image processing unit 38 performs predetermined image processing such as volume rendering, MPR (Multi Planar Reconstruction), and MIP (Maximum Intensity Projection) for the data received from the volume data generation unit 36. The display processing unit 40 executes various types of processing associated with a dynamic range, luminance (brightness), contrast, γ curve correction, RGB conversion, and the like for various types of image data generated/processed by the image processing unit 38.

The control processor 39 has the function of an information processing apparatus (computer) and controls the operation of this ultrasonic diagnostic apparatus main body. The storage unit 41 stores diagnosis information (patient IDs, findings by doctors, and the like), a diagnostic protocol, transmission/reception conditions, an image processing program, and other data groups. The interface unit 42 is an interface concerning the input device 13, a network, and an external storage device (not shown). It is also possible to transfer data such as ultrasonic images, analysis results, and the like obtained by this apparatus to other apparatuses via the interface unit 42 and a network.

(Ultrasonic Probe Having FPC Multilayer Body)

Figure 3:
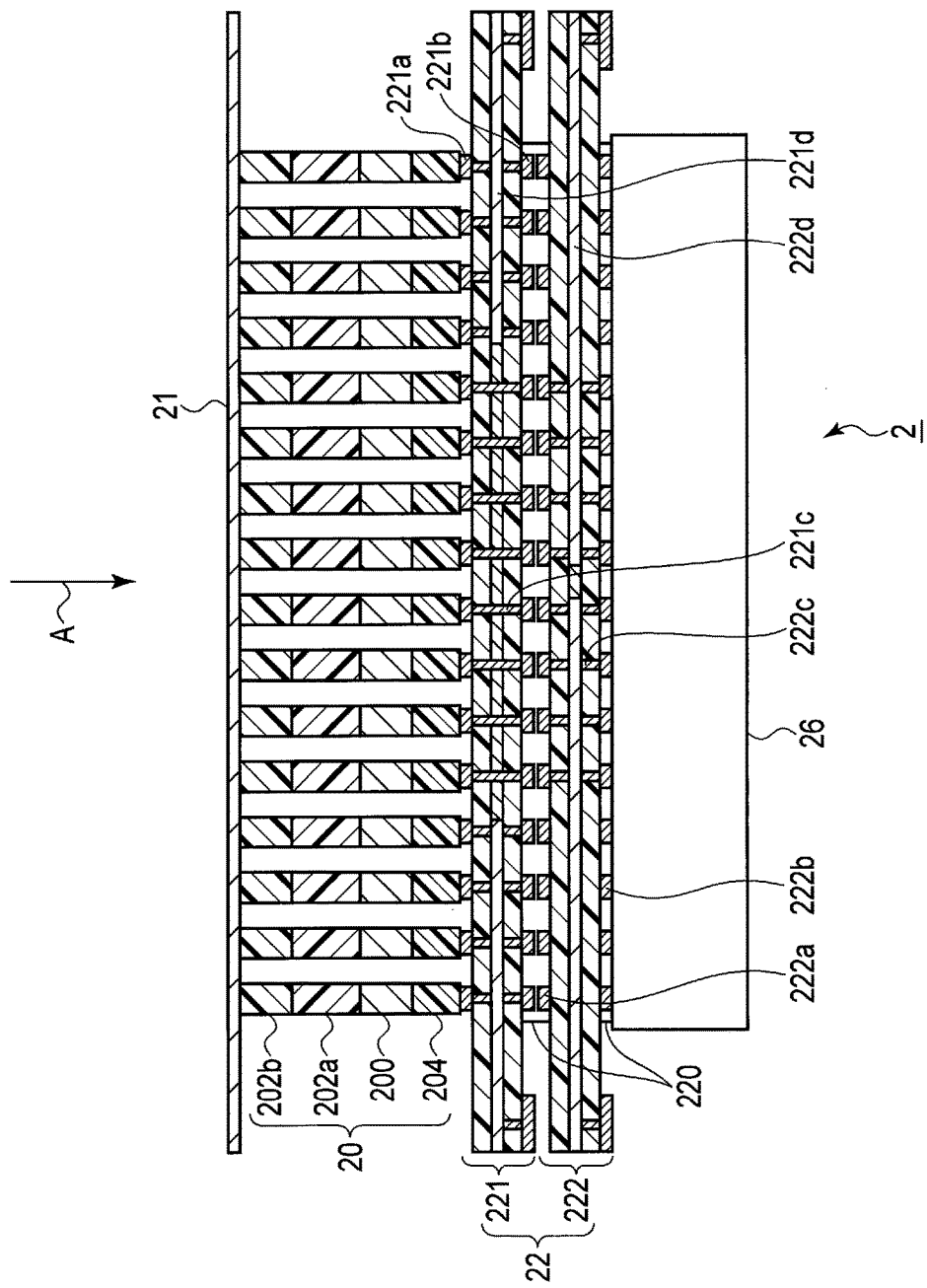
FIG. 3 is a side view of the ultrasonic probe 2 according to this embodiment.

FIG. 2 is a plan view of the ultrasonic probe 2 according to this embodiment when viewed from the ultrasonic wave irradiation surface side (from an arrow A in FIG. 3). FIG. 3 is a side view of the ultrasonic probe 2 according to the embodiment. As shown in FIGS. 2 and 3, the ultrasonic probe 2 includes a plurality of ultrasonic transducers 20, a GND layer 21 functioning as a GND electrode, an FPC multilayer body 22, a backplane member 26, and an electronic circuit board 28. Note that the plurality of ultrasonic transducers 20 are arrayed on a two-dimensional plane to form a transducer array. In order to embody wiring extraction from each ultrasonic transducer by using the FPC multilayer body 22, the ultrasonic transducers are classified into the first and second groups under spatial conditions (a generalized arrangement of the arrangement will be described later) in FIG. 2. Typically, the manner of classifying ultrasonic transducers into groups depends on the orientations of circuit boards connected via the FPC multilayer body 22. In the embodiment, ultrasonic transducers are classified assuming that the circuit boards are arranged in the longitudinal direction as shown in FIG. 2. However, this example is not exhaustive, and the manner of classifying ultrasonic transducers can be changed, as needed, in accordance with the orientations of circuit boards.

Each ultrasonic transducer 20 includes a dielectric body 200, acoustic matching layers 202*a* and 202*b*, and an intermediate layer 204. The dielectric body 200 transmits ultrasonic waves in a desired direction in a scan region based on a driving signal from electronic circuitry on the electronic circuit board 28, and converts reflected waves from the object into an electrical signal. The acoustic matching layers 202*a* and 202*b* are provided for the piezoelectric body to make ultrasonic energy efficiently propagate. The intermediate layer 204 is provided on the opposite side to the acoustic emission surface of the dielectric body 200 and has an acoustic impedance sufficiently higher than those of the dielectric body 200 and conductive layer to suppress the influence of the FPC multilayer body 22 on the vibration characteristic of the ultrasonic transducer. The intermediate layer 204 can minimize the acoustic influence of the conductive layer and improve the homogeneity of the overall array.

The GND layer 21 is connected to the GND electrode (not shown) of the electronic circuit board 28 via the GND layer (not shown) of the FPC multilayer body 22. The backplane member 26 attenuates weak ultrasonic waves emitted from each ultrasonic transducer backward. Electronic circuitry used for transmission/reception is mounted on the electronic circuit board 28. As shown in, for example, FIGS. 3 and 5, the electronic circuit board 28 is arranged vertical to the array surface (drawing surface) of the ultrasonic transducer array.

Each FPC multilayer body 22 includes a first FPC layer 221, a second FPC layer 222, and an adhesive layer (ACF) 220 which bonds the first FPC layer 221 to the second FPC layer 222 in a region corresponding to the width of the transducer array. The backplane member 26 and the FPC multilayer body 22 are bonded to each other with a general epoxy adhesive material. The first FPC layer 221 and the second FPC layer 222 are not bonded to each other outside the region corresponding to the width of the transducer array, and hence can be independently and freely maneuvered while maintaining flexibility. For example, the first FPC layer 221 and the second FPC layer 222 are bent at right angles at the end portions of the backplane member 26 and connected to the electronic circuit boards 28 again at the end portions via exposed board connection pads (not shown).

The first FPC layer 221 includes a plurality of first upper surface electrode pads 221a, first lower surface electrode pads 221b, a plurality of first signal wire patterns 221d, and a plurality of first through holes 221c. For the sake of descriptive convenience, for example, the first upper surface electrode pads 221a spatially corresponding to ultrasonic transducers belonging to the nth group will be simply referred to as "the first upper surface electrode pads 221a belonging to the nth group" hereinafter. The same applies to the lower surface electrode pads, the signal wire pads, and the through holes.

The plurality of first upper surface electrode pads 221a are formed on the multilayer surface (upper surface) of the transducer array in an array and at a pitch, which array and pitch spatially correspond to the plurality of ultrasonic transducers (their electrodes) so as to be electrically connected to the ultrasonic transducers in a one-to-one relationship. Note that the electrode of each ultrasonic transducer is connected to a corresponding one of the first upper surface electrode pads 221a by a means such as pressure bonding. However, this technique is not exhaustive. For example, this process can be implemented by a means using an adhesive layer (ACF), a reflow means using a solder, and other equivalent means.

The plurality of first lower surface electrode pads 221b are formed on the lower surface of the transducer array on the opposite side to the multilayer surface of the transducer array in an array and at a pitch, which array and pitch spatially correspond to the plurality of ultrasonic transducers (their electrodes).

The plurality of first through holes 221c extend through the upper surface to the lower surface in an array and at a pitch, which array and pitch spatially correspond to the plurality of ultrasonic transducers (their electrodes) so as to electrically connect the first upper surface electrode pads 221a to the first lower surface electrode pads 221b in a one-to-one relationship.

The plurality of first signal wire patterns 221d are wirings extracted from the first upper surface electrode pads 221a, of the plurality of first upper surface electrode pads 221a, which belong to the first group to the end portions of the first FPC layer 221 via the first through holes 221c, and electrically connect the first upper surface electrode pads 221a belonging to the first group to electronic circuits.

Note that the first lower surface electrode pads 221b belonging to the first group are not connected to the first signal wire pattern 221d either, and hence are also electrically independent of any of the ultrasonic transducers.

The second FPC layer 222 includes a plurality of second upper surface electrode pads 222a, a plurality of second lower surface electrode pads 222b, a plurality of second through holes 222c, and a plurality of second signal wire patterns 222d.

The plurality of second upper surface electrode pads 222a are formed on the multilayer surface (upper surface) of the second FPC layer 222 in an array and at a pitch, which array and pitch spatially correspond to the plurality of ultrasonic transducers (their electrodes). In addition, each of the second upper surface electrode pads 222a (second FPC layer 222) is made electrically conductive to a spatially corresponding one of the second lower surface electrode pads 222b. As a result, the second upper surface electrode pads 222a, of the plurality of second upper surface electrode pads 222a, which belong to the second group are electrically connected to the ultrasonic transducers belonging to the second group.

The plurality of second lower surface electrode pads 222b are formed on the lower surface on the opposite side to the upper surface, on which the first FPC layer 221 is stacked, in an array and at a pitch, which array and pitch spatially correspond to the plurality of ultrasonic transducers (their electrodes).

The plurality of second through holes 222c extend through the upper surface to the lower surface in an array and at a pitch, which array and pitch spatially correspond to ultrasonic transducers (their electrodes) which belong to at least the second group so as to electrically connect the second upper surface electrode pads 222a belonging to at least the second group to the second lower surface electrode pads 222b belonging to at least the second group in a one-to-one relationship.

The plurality of second signal wire patterns 222d are wirings extracted from the second upper surface electrode pads 222a belonging to the second group to the end portions of the second FPC layer 222 via the second through holes 222c, and electrically connect the second upper surface electrode pads 222a belonging to the second group to electronic circuits. As a result, the ultrasonic transducers belonging to the second group are electrically connected to the electronic circuits via the second signal wire patterns 222d.

Note that the second lower surface electrode pads 222b belonging to the first group of the second FPC layer 222 are connected to neither through holes nor signal wire patterns. Therefore, the second lower surface electrode pads 222b belonging to the first group are electrically independent of any of the second upper surface electrode pads 222a or also the ultrasonic transducers.

In addition, the first FPC layer 221 and the second FPC layer 222 are bonded to each other by using, for example, the adhesive layer (ACF) 220 such that the electrodes facing each other are rendered electrically conductive. Note that the way to bond the first FPC layer 221 to the second FPC layer 222 is not limited to the example using the adhesive layer 220. For example, this process can be implemented by pressure bonding, soldering connection, and other equivalent means.

In addition, the first FPC layer 221 shown as an example in FIGS. 2 and 3 includes the upper surface layer having the upper surface on which the plurality of first upper surface electrode pads 221a are formed, the lower surface layer having the lower surface on which the plurality of first lower surface electrode pads 221b are formed, and the intermediate layer formed between the upper surface layer and the lower surface layer and having the plurality of first signal wire patterns 221d. However, this example is not exhaustive. For example, when there are many ultrasonic transducers, a plurality of intermediate layers may be formed, and wirings may be extracted stepwise from the first upper surface electrode pads 221a on the respective intermediate layers. The same applies to the second FPC layer 221.

The FPC multilayer body 22 of the ultrasonic probe 2 according to this embodiment is not limited to the example having the two FPC layers exemplarily shown in FIGS. 2 and 3. The FPC multilayer body 22 can also be provided with more FPC layers in accordance with the number of ultrasonic transducers.

Figure 5:
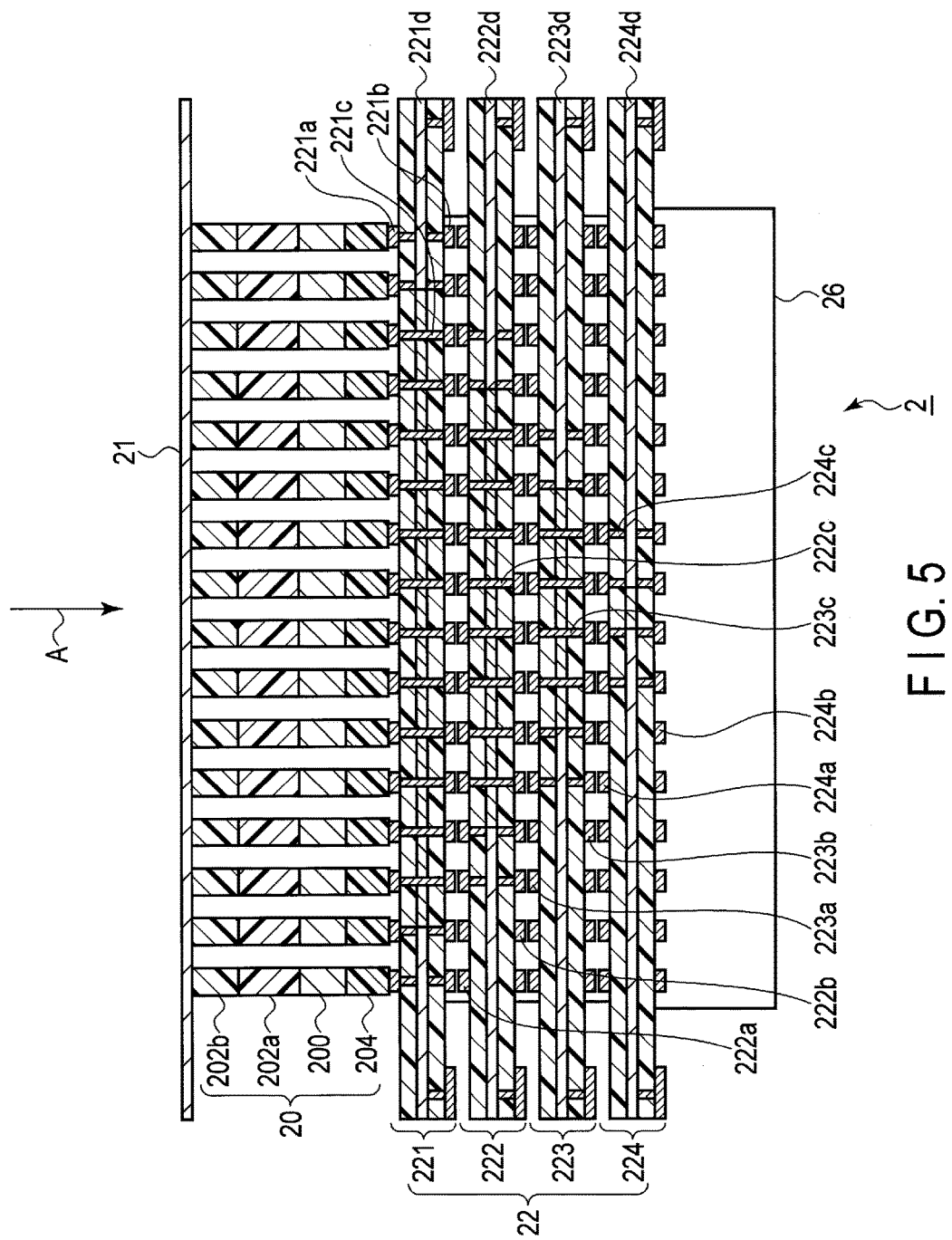
FIG. 5 is a side view of the ultrasonic probe 2 shown in FIG. 4, exemplarily showing the FPC multilayer body 22 having four FPC layers.

FIG. 4 is a plan view of the ultrasonic probe 2 to which the FPC multilayer body 22 having four FPC layers is applied when viewed from the ultrasonic wave irradiation surface side (from an arrow A in FIG. 5). Referring to FIG. 4, the transducer array is classified into the first to fourth groups with reference to the orientation of the circuit board. FIG. 5 is a side view of the ultrasonic probe 2 shown in FIG. 4, exemplarily showing the FPC multilayer body 22 having four FPC layers. Only arrangements different from those shown in FIGS. 2 and 3 will be described below.

The FPC multilayer body 22 of the ultrasonic transducer 20 includes the first FPC layer 221, the second FPC layer 222, a third FPC layer 223, a fourth FPC layer 224, and the adhesive layers (ACFs) 220 which bond the respective FPC layers to each other in a region corresponding to the width of the transducer array.

The first through holes 221c belonging to the second to fourth groups on the first FPC layer 221 electrically connect the first upper surface electrode pads 221a belonging to the second to fourth groups to the first lower surface electrode pads 221b belonging to the second to fourth groups in a one-to-one relationship.

The second upper surface electrode pads 222a belonging to the second to fourth groups on the second FPC layer 222 are electrically connected to the ultrasonic transducers belonging to the second to fourth groups as a result of rendering the second upper surface electrode pads 222a electrically conductive to the spatially corresponding first lower surface electrode pads 221b (of the first FPC layer 221). The plurality of second through holes 222c extend through the upper surface to the lower surface in an array and at a pitch, which array and pitch spatially correspond to the ultrasonic transducers (their electrodes) belonging to the second, third, and fourth groups so as to electrically connect the second upper surface electrode pads 222a belonging to the second, third, and fourth groups to the second lower surface electrode pads 222b belonging to the second, third, and fourth groups in a one-to-one relationship. The plurality of second signal wire patterns 222d are wirings extracted from the second upper surface electrode pads 222a belonging to the second group to the end portions of the second FPC layer 222 via the second through holes 222c, and electrically connect the second upper surface electrode pads 222a belonging to the second group to electronic circuits. Note that the second lower surface electrode pads 222b belonging to the first group are electrically independent of any of the second upper surface electrode pads 222a or also the ultrasonic transducers.

A plurality of third upper surface electrode pads 223a on the upper surface of the third FPC layer 223 are formed in an array and at a pitch, which array and pitch spatially correspond to a plurality of ultrasonic transducers, and so are third lower surface electrode pads 223b on the lower surface. The third upper surface electrode pads 223a belonging to the third and fourth groups are electrically connected to the ultrasonic transducers belonging to the third and fourth groups as a result of bonding the second FPC layer 222 to the third FPC layer 223. A plurality of third through holes 223c extend through the upper surface to the lower surface in an array and at a pitch, which array and pitch spatially correspond to the ultrasonic transducers belonging to the third and fourth groups, and electrically connect the third upper surface electrode pads 223a belonging to the third and fourth groups to the third electrode pads 223b belonging to the third and fourth groups in a one-to-one relationship. A plurality of third signal wire patterns 223d are wirings extracted from the third upper surface electrode pads 223a belonging to the third group to the end portions of the third FPC layer 223 via the third through holes 223c, and electrically connect the third upper surface electrode pads 223a belonging to the third group to the electronic circuits. Note that the third lower surface electrode pads 223b belonging to the first and second groups are electrically independent of any of the third upper surface electrode pads 223a or also the ultrasonic transducers.

A plurality of fourth upper surface electrode pads 224a on the upper surface of the fourth FPC layer 224 are formed in an array and at a pitch, which array and pitch spatially correspond to a plurality of ultrasonic transducers, and so are a plurality of fourth lower surface electrode pads 224b on the lower surface. The fourth upper surface electrode pads 224a belonging to the fourth group are electrically connected to the ultrasonic transducers belonging to the fourth group as a result of bonding the third FPC layer 223 to the fourth FPC layer 224. A plurality of fourth through holes 224c extend through the upper surface to the lower surface in an array and at a pitch, which array and pitch spatially correspond to the ultrasonic transducers belonging to the fourth group, and electrically connect the fourth upper surface electrode pads 224a belonging to the fourth group to the fourth lower surface electrode pads 224b belonging to the fourth group in a one-to-one relationship. A plurality of signal wire patterns 224d are wirings extracted from the fourth upper surface electrode pads 224a belonging to the fourth group to the end portions of the fourth FPC layer 224 via the through holes 224c, and electrically connect the fourth upper surface electrode pads 224a belonging to the fourth group to the electronic circuits. Note that the fourth lower surface electrode pads 224b belonging to the first, second, and third groups are electrically independent of any of the fourth upper surface electrode pads 224a or also the ultrasonic transducers.

As described above, the ultrasonic probe 2 to which the FPC multilayer body 22 having the four FPC layers is applied can also be implemented.

Note that, in principle, the ultrasonic probe according to this embodiment allows an unlimited increase in the number of FPC layers together with the classification of the ultrasonic probe into a plurality of groups. That is, generalization can be implemented such that a plurality of ultrasonic transducers are classified into n groups, and wirings from the ultrasonic transducers belonging to the respective groups are extracted from corresponding FPC layers of the FPC multilayer body 22 having n layers (where n is a natural number satisfying n≥2). Even if, however, the end portions of each FPC layer are not bonded, an increase in the number of FPC layers to be stacked will increase the rigidity of the end portions of the FPC multilayer body 22, resulting in difficulty in handling. It is therefore preferable to adjust the number of FPC layers within the range in which the flexibility of the end portions of the FPC multilayer body 22 can be maintained.

Figure 6:
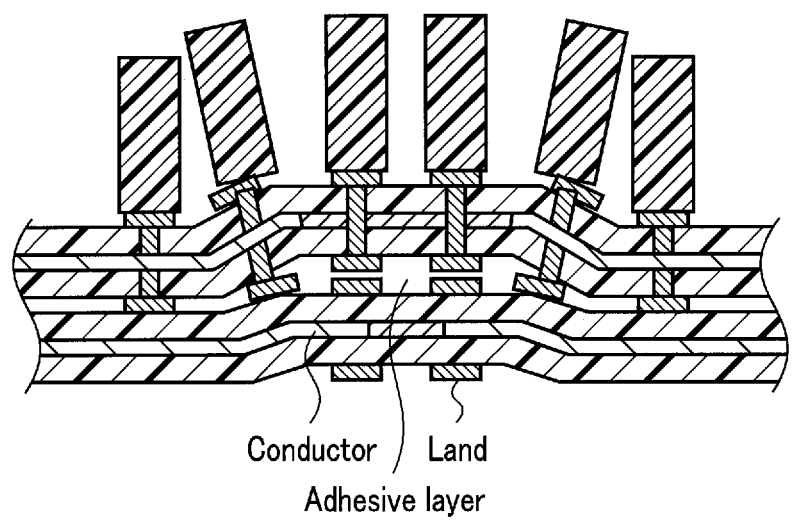
FIG. 6 is a view for explaining the effects of an ultrasonic probe according to this embodiment.

According to the arrangement described above, each FPC layer of the FPC multilayer body 22 has upper surface connection pads and lower surface electrode pads, with a uniform level being maintained, at positions spatially corresponding to the respective ultrasonic transducers. Therefore, for example, as shown in FIG. 6, no irregularity occurs regardless of the presence/absence of pads at the positions spatially corresponding to the respective ultrasonic transducers. This makes it possible to make the FPC multilayer body 22 have a uniform thickness (height) and easily and accurately connect the ultrasonic transducer array to the FPC multilayer body. This arrangement provides practical benefits especially when obtaining electrical connection by pressure bonding or the like.

In addition, the ultrasonic probe using the FPC multilayer body according to this embodiment allows easy and accurate connection between the ultrasonic transducer array and the FPC multilayer body without requiring any complicated manufacturing processes and can greatly increase the number of ultrasonic transducers to be mounted. This can increase the number of transmission and reception signals (channels) and reduce side lobes and grating lobes, thereby improving the image quality of ultrasonic images.

In addition, the plurality of FPC layers constituting the FPC multilayer body 22 are integrally formed only in the region corresponding to the width of the ultrasonic transducer array but are not bonded to each other and are separated from each other outside the region corresponding to the width of the ultrasonic transducer array. Therefore, the FPC layers can be connected to an electronic circuit board independently of each other or different electronic circuit boards while the flexibility of each FPC layer is maintained. This can reduce the area of each electronic circuit board and implement an arrangement in which a plurality of electronic circuit boards are stacked in the thickness direction. It is therefore possible to implement an enormous number of electronic circuits while suppressing an area. Furthermore, since ICs need not be directly mounted on transducers, there is no need to develop a dedicated IC (ASIC) for each different specification. Moreover, it is possible to process all arrays by using a plurality of ICs while suppressing the size (area) of one IC. This can reduce a development cost and manufacturing cost. It is possible to reduce the number elements which are not connected along the use of the sparse technique and greatly reduce the gaps accompanying module division, thereby implement high performance.

Note that the present invention is not limited to the above embodiments, and constituent elements can be modified and embodied in the execution stage within the spirit and scope of the invention. For example, the following are concrete modifications.

Figure 7:
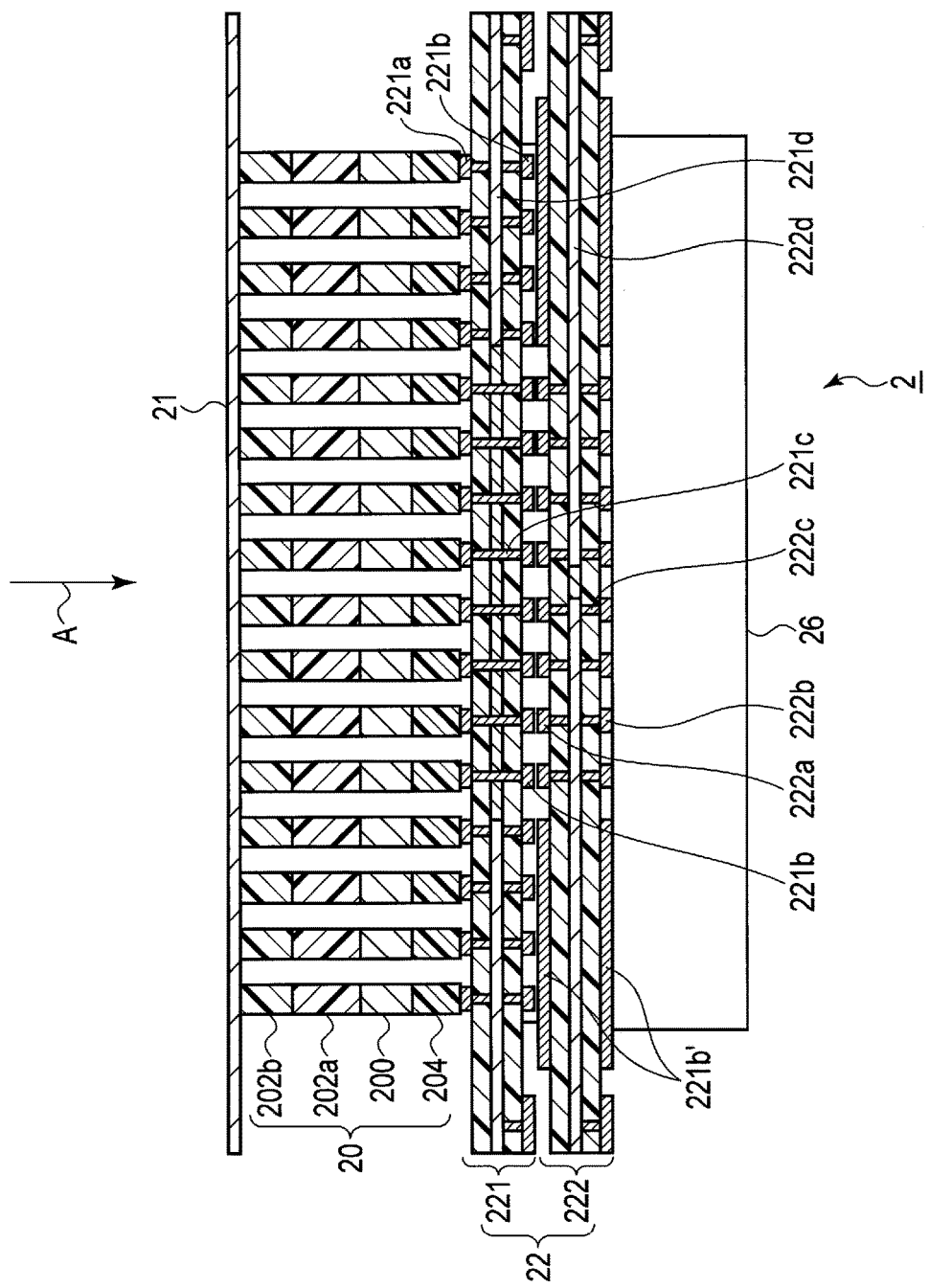
FIG. 7 is a view showing an example of replacing second lower surface electrode pads 222b belonging to the first group shown in FIG. 3 with coverlay (resin layers).
Figure 8:
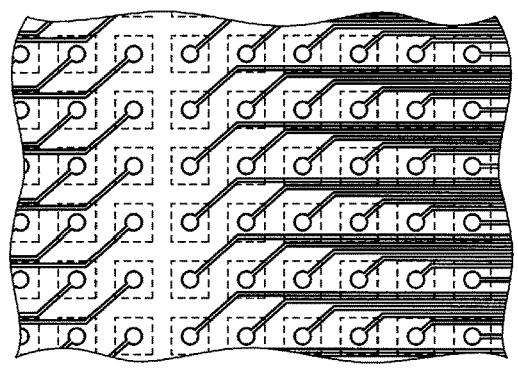
FIG. 8 is a view for explaining an example of a technique of connecting electronic circuits to each ultrasonic transducer in a conventional ultrasonic probe.
Figure 9:
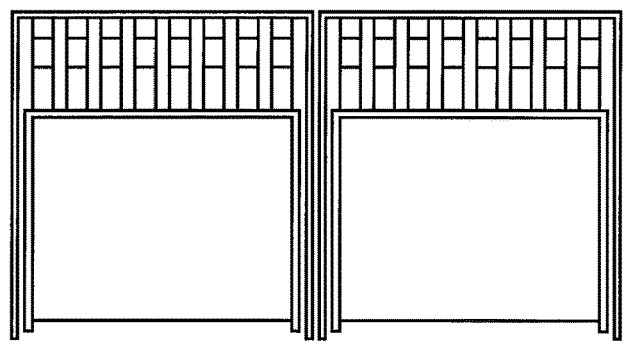
FIG. 9 is a view for explaining another example of a technique of connecting electronic circuits to each ultrasonic probe in a conventional ultrasonic probe.
Figure 10:
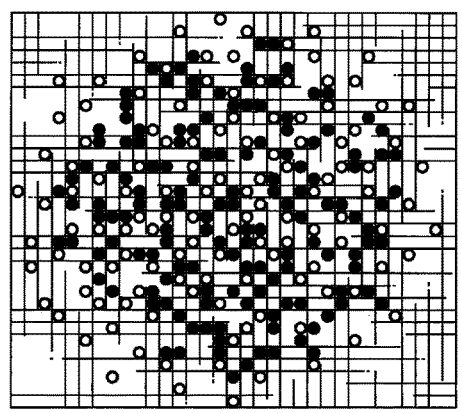
FIG. 10 is a view for explaining still another example of a technique (sparse technique) of connecting electronic circuits to each ultrasonic probe in a conventional ultrasonic probe.
Figure 11:
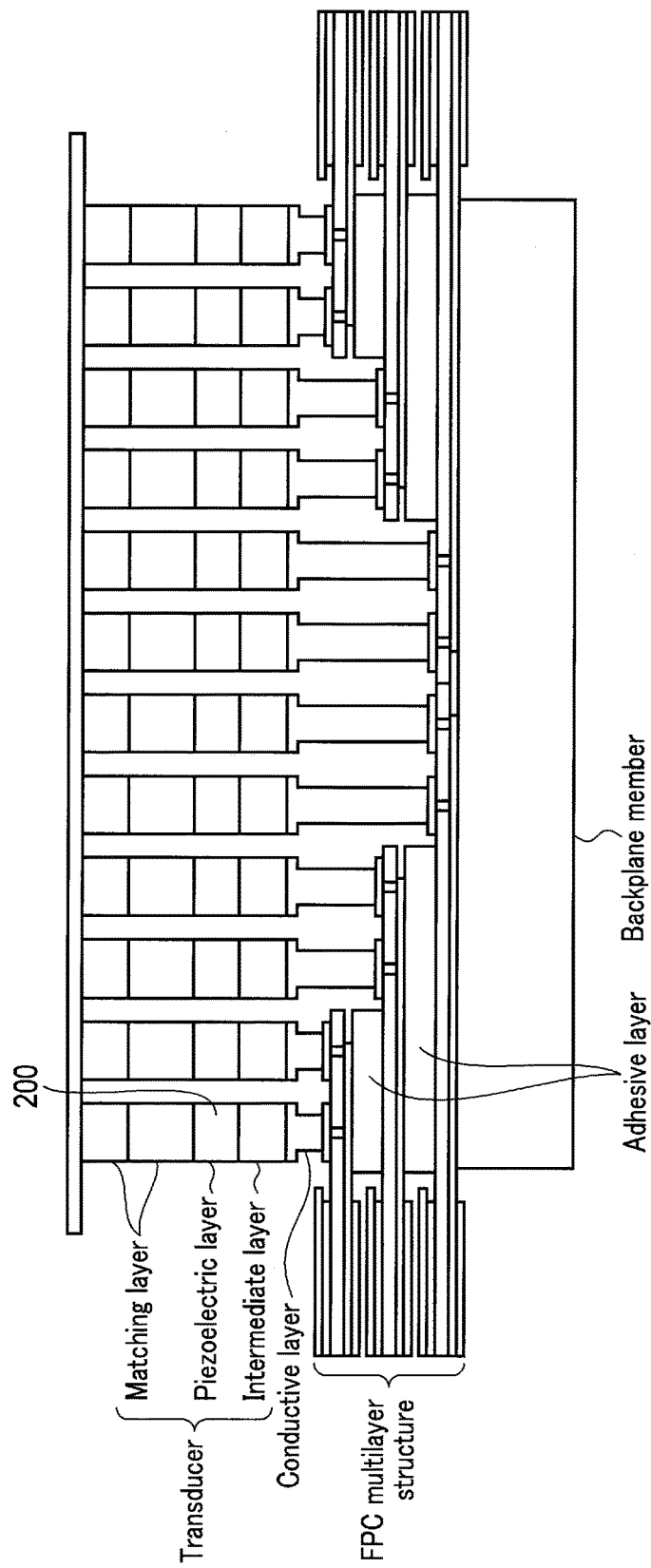
FIG. 11 is a view for explaining still another example of a technique of connecting electronic circuits to each ultrasonic probe in a conventional ultrasonic probe.
Figure 12:
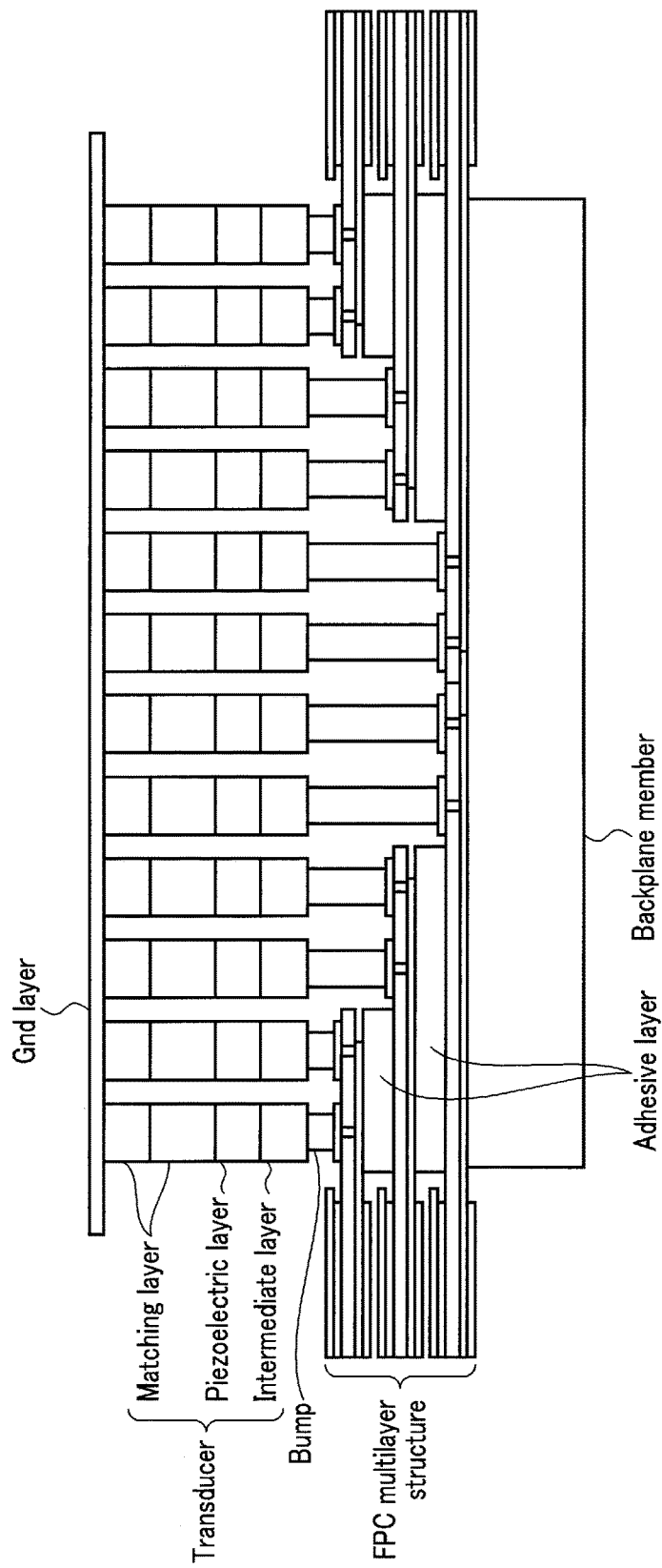
FIG. 12 is a view for explaining still another example of a technique of connecting electronic circuits to each ultrasonic probe in a conventional ultrasonic probe.

(1) For example, the second lower surface electrode pads 222b belonging to the first group, the second lower surface electrode pads 222b belonging to the first group which are shown in FIG. 5, the third lower surface electrode pads 223b belonging to the first and second groups, and the fourth lower surface electrode pads 224b belonging to the first, second, and third groups are electrically independent, and do not contribute to control of the ultrasonic transducers. Therefore, these independent electrode pads can be replaced with a resin such as coverlay. FIG. 7 shows an example of replacing the second lower surface electrode pads 222b belonging to the first group shown in FIG. 3 with coverlay (resin layers such as solder resist layers) 221b'. Note however that it is necessary to match the thickness of each resin layer with the thickness of the electrode layer formed on the same surface. Therefore, using the independent second electrode pads as shown in FIGS. 3 and 5 and the like is advantageous in terms of manufacturability.

(2) The above embodiments have described the ultrasonic probe used for an ultrasonic diagnostic apparatus as an example. However, this example is not exhaustive, and the arrangements according to the embodiments of this application can be applied to the ultrasonic probe of an ultrasonic sensor used for construction and the like.

(3) The above embodiments have described the application of the two-dimensional ultrasonic probe having the flat ultrasonic transmission/reception surface as an example. However, this example is not exhaustive, and the embodiments can also be applied to a one- or two-dimensional ultrasonic probe having a curved ultrasonic transmission/reception surface like an abdominal convex probe. In such a case, for example, in the case shown in FIG. 3, the FPC multilayer body 22 (that is, the first FPC layer 221 and the second FPC layer 222) is configured to form a curved ultrasonic transmission/reception surface or curve along a curvature. Likewise, for example, in the case shown in FIG. 5, the FPC multilayer body 22 (that is, the first FPC layer 221, the second FPC layer 222, the third FPC layer 223, the third FPC layer 223, and the fourth FPC layer 224) is configured to form a curved ultrasonic transmission/reception surface or curve along a curvature.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

The invention claimed is:

1. An ultrasonic probe comprising an ultrasonic transducer array formed by arraying a plurality of ultrasonic transducers provided with electrodes on end faces and a multilayer body configured to extract electric wirings from the respective electrodes, wherein the plurality of ultrasonic transducers are classified into at least a first group and a second group, the multilayer body includes at least a first flexible printed circuits (FPC) layer on which the ultrasonic transducer array is stacked and a second FPC layer on which the first FPC layer is stacked, the first FPC layer includes at least a plurality of first upper surface connecting portions provided on an upper surface of the first FPC layer, on which the ultrasonic transducer array is stacked, so as to spatially correspond to the plurality of ultrasonic transducers, and electrically connected to the plurality of electrodes, a plurality of first lower surface connecting portions provided on a lower surface of the first FPC layer on an opposite side to the upper surface of the first FPC layer so as to spatially correspond to the plurality of ultrasonic transducers, a plurality of first through holes formed throughout from the upper surface of the first FPC layer to the lower surface of the first FPC layer so as to electrically connect the plurality of upper surface connecting portions connected to the electrodes of the ultrasonic transducers belonging to at least the second group to the plurality of first lower surface connecting portions, and first signal wirings configured to extract electric wirings from the first upper surface connecting portions connected to the electrodes of the ultrasonic transducers belonging to the first group, and the second FPC layer includes at least a plurality of second upper surface connecting portions provided on an upper surface of the second FPC layer, on which the first FPC layer is stacked, so as to spatially correspond to the plurality of ultrasonic transducers and electrically connected to the plurality of first lower surface connecting portions, a plurality of second lower surface connecting portions provided on a lower surface of the second FPC layer on an opposite side to the upper surface of the second FPC layer so as to spatially correspond to the plurality of ultrasonic transducers, and second signal wirings configured to extract electric wirings from the second upper surface connecting portions connected to the electrodes of the ultrasonic transducers belonging to the second group, wherein at least one of the plurality of first lower surface connecting portions is electrically independent from the plurality of ultrasonic transducers, and at least one of the plurality of second upper surface connecting portions and at least one of the plurality of second lower surface connecting portions are electrically independent from each other.

2. The ultrasonic probe of claim 1, wherein the plurality of ultrasonic transducers are classified into at least the first group, the second group, and a third group, the multilayer body includes at least the first FPC layer, the second FPC layer, and a third FPC layer on which the second FPC layer is stacked, the second FPC layer further includes a plurality of second through holes formed throughout from the upper surface of the second FPC layer to the lower surface of the second FPC layer so as to electrically connect the second upper surface connecting portions connected to the electrodes of the ultrasonic transducers belonging to at least the third group to the second lower surface connecting portions, and the third FPC layer includes at least a plurality of third upper surface connecting portions provided on an upper surface of the third FPC layer, on which the second FPC layer is stacked, so as to spatially correspond to the plurality of ultrasonic transducers and electrically connected to the plurality of second lower surface connecting portions, a plurality of third lower surface connecting portions provided on a lower surface of the third FPC layer on an opposite side to the upper surface of the third FPC layer so as to spatially correspond to the plurality of ultrasonic transducers, and third signal wirings configured to electrically connect the third upper surface connecting portions connected to the electrodes of the ultrasonic transducers belonging to the third group, wherein at least one of the plurality of third upper surface connecting portions and at least one of the plurality of third lower surface connecting portions are electrically independent from each other.

3. The ultrasonic probe of claim 2, wherein the plurality of ultrasonic transducers are classified into at least the first group to an nth group (where n is a natural number satisfying n≥4), the multilayer body includes at least the first FPC layer to an nth FPC layer respectively corresponding to the first group to the nth group, an (n−1)th FPC layer among the first FPC layer to the nth FPC layer includes a plurality of (n−1)th through holes formed throughout from an upper surface of the (n−1)th FPC layer to a lower surface of the (n−1)th FPC layer so as to electrically connect a plurality of (n−1)th upper surface connecting portions connected to the electrodes of the ultrasonic transducers belonging to at least the nth group to a plurality of (n−1)th lower surface connecting portions, and the nth FPC layer includes at least a plurality of nth upper surface connecting portions provided on an upper surface of the nth FPC layer, on which the (n−1)th FPC layer is stacked, so as to spatially correspond to the plurality of ultrasonic transducers and electrically connected to the plurality of (n−1)th lower surface connecting portions, a plurality of nth lower surface connecting portions provided on a lower surface of the nth FPC layer on an opposite side to the upper surface of the nth FPC layer so as to spatially correspond to the plurality of ultrasonic transducers, and nth signal wirings configured to electrically connect the nth upper surface connecting portions connected to the electrodes of the ultrasonic transducers belonging to the nth group, wherein at least one of the plurality of (n−1)th lower surface connecting portions is electrically independent from the plurality of ultrasonic transducers, and at least one of the plurality of nth upper surface connecting portions and at least one of the plurality of nth lower surface connecting portions are electrically independent from each other.

4. The ultrasonic probe of claim 1, wherein the plurality of upper surface connecting portions and the plurality of lower surface connecting portions of each of the FPC layers each maintain the same level, and the respective FPC layers have substantially a uniform thickness.

5. The ultrasonic probe of claim 1, wherein the respective FPC layers are bonded to each other in a region corresponding to a width of the ultrasonic transducer array, and are not bonded to each other outside the region corresponding to the width of the ultrasonic transducer array.

6. The ultrasonic probe of claim 1, wherein each of the FPC layers includes an upper surface layer on which the corresponding plurality of upper surface connecting portions are formed, a lower surface layer on which the corresponding plurality of lower surface connecting portions are formed, and at least one intermediate layer on which the corresponding signal wirings are formed.

7. The ultrasonic probe of claim 1, wherein the plurality of upper surface connecting portions and the plurality of lower surface connecting portions on each of the FPC layers are formed from the same conductive material.

8. The ultrasonic probe of claim 1, wherein the plurality of upper surface connecting portions and the plurality of lower surface connecting portions which are not electrically connected to the corresponding signal wirings on each of the FPC layers are formed from a resin.

9. The ultrasonic probe of claim 1, wherein the respective FPC layers are pressure bonded to each other while spatial correspondence between the plurality of second upper surface connecting portions and the plurality of first lower surface connecting portions is maintained.

10. The ultrasonic probe of claim 1, wherein the respective FPC layers are connected to each other with an adhesive layer while spatial correspondence between the plurality of second upper surface connecting portions and the plurality of first lower surface connecting portions is maintained.

11. The ultrasonic probe of claim 1, further comprising electronic circuitry connected to the first upper surface connecting portions or the second upper surface connecting portions.

12. The ultrasonic probe of claim 1, wherein the ultrasonic transducer array comprises a one dimensional array having the plurality of ultrasonic transducers arrayed one dimensionally.

13. The ultrasonic probe of claim 1, wherein the ultrasonic transducer array comprises a one dimensional array having the plurality of ultrasonic transducers arrayed two dimensionally.

14. The ultrasonic probe of claim 1, wherein the ultrasonic transducer array is obtained by arraying the plurality of ultrasonic transducers such that an ultrasonic transmission/reception surface is a curved surface, and the first FPC layer and the second FPC layer are curved along the curved surface.

\* \* \* \* \*